US008822932B2

(12) United States Patent
Scoville et al.

(10) Patent No.: US 8,822,932 B2
(45) Date of Patent: Sep. 2, 2014

(54) APPARATUS AND SYSTEM FOR INSPECTING STRUCTURES

(75) Inventors: Daniel Jay Scoville, Houston, TX (US); Rajashekar Venkatachalam, State College, PA (US); Christopher Jay Morse, North Prairie, WI (US)

(73) Assignee: General Electric Company, Schenectady, NY (US)

( * ) Notice: Subject to any disclaimer, the term of this patent is extended or adjusted under 35 U.S.C. 154(b) by 213 days.

(21) Appl. No.: 13/351,876

(22) Filed: Jan. 17, 2012

(65) Prior Publication Data
US 2013/0181136 A1 Jul. 18, 2013

(51) Int. Cl.
*G01T 1/161* (2006.01)
(52) U.S. Cl.
USPC .................................................. 250/363.02
(58) Field of Classification Search
USPC .................................................. 250/363.02
See application file for complete search history.

(56) References Cited

U.S. PATENT DOCUMENTS

| | | | |
|---|---|---|---|
| 6,173,606 B1 * | 1/2001 | Mosley | 73/152.16 |
| 7,244,943 B2 | 7/2007 | Seppi | |
| 7,291,842 B2 | 11/2007 | Zentai et al. | |
| 7,745,797 B1 | 6/2010 | Liu et al. | |
| 2002/0080265 A1 * | 6/2002 | Hoffman | 348/374 |
| 2006/0124354 A1 * | 6/2006 | Witte | 175/40 |
| 2011/0133085 A1 | 6/2011 | Konkle et al. | |
| 2013/0168554 A1 * | 7/2013 | Howe et al. | 250/358.1 |

OTHER PUBLICATIONS

Digital Radiography Using Digital Detector Arrays Fulfills Critical Applications for Offshore Pipelines, Edson Vasques Moreira, et al., Hindawi Publishing Corporation, vol. 2010, Article ID 894643, 8 pages, Jun. 2010.

* cited by examiner

*Primary Examiner* — David Porta
*Assistant Examiner* — Hugh H Maupin
(74) *Attorney, Agent, or Firm* — Hiscock & Barclay LLP

(57) ABSTRACT

This disclosure describes an apparatus and a system for inspection of deepwater assets, e.g., pipes and pipelines that traverse the ocean floor. In one embodiment, the apparatus includes a housing that retains a compensation fluid therein to form a fluidic environment. A digital detector resides in the fluidic environment. The digital detector can generate digital images in response to radiation that penetrate though the deepwater asset and impinges on components of the digital detector. In one embodiment, the digital detector utilizes one or more seal members to secure the components together. The seal members may be permeable and/or impermeable to the compensation fluid thereby preventing and/or permitting migration of the compensation fluid between certain components of the digital detector.

20 Claims, 5 Drawing Sheets

APPARATUS AND SYSTEM FOR INSPECTING STRUCTURES

BACKGROUND OF THE INVENTION

The subject matter disclosed herein relates to inspection and image acquisition and, more particularly, to embodiments of an apparatus and a system that can generate digital images of an asset located in environments at high pressures, e.g., pressures consistent with extreme depths below sea level.

Inspection of assets including, for example, pipes and pipelines that reside underwater, is important to identify areas of the asset that may require pre-emptive maintenance or that represent a risk of failure. However, in many cases, these assets are found in environments that are not hospitable for humans to perform visual inspection. Nor could visual inspection, whether by human or remote visual inspection equipment, even ascertain defects, flaws, and other anomalies that are the source of failure in the asset because such anomalies may occur beneath the exterior surface of the asset. Thus, proper inspection may require use of special inspection equipment that can provide a view, or image, of the internal structure and health of the asset.

Examples of this special inspection equipment include conventional x-ray and ultrasonic devices, both of which can penetrate the exterior surface of the asset to generate an image of the internal structure of the asset. However, neither of these types of devices are particularly well suited to inspect deepwater assets. To use ultrasonic devices for inspecting pipes underwater, for example, the ultrasonic device must be positioned proximate, and often in contact with, the surface of the asset. Unfortunately, these surfaces are often covered by protective coverings (e.g., insulation) or are generally not readily available without removal and/or manipulation of the protective covering from the area on which the ultrasonic device is to contact.

X-ray devices, on the other hand, can penetrate through the protective coverings as well as any peripheral structure to capture images of the internal structure of the asset. However, most conventional x-ray devices require radiation to penetrate the asset and to expose imaging plates. These imaging plates must then traverse the ocean depths from the deepwater pipeline to the surface where the imaging plate can be viewed. This procedure is neither cost effective nor efficient, let alone practical when x-ray devices are used in connection with assets that are located many miles below the ocean surface.

Another example of inspection equipment utilizes digital radiography to generate images of the asset. These digital radiography imaging systems generally use x-ray radiation to interact with digital flat panel x-ray detectors. In response to the radiation, the x-ray detectors generate digital signals that can traverse conduits from the asset to the ocean surface where digital processing equipment generates digital images. Such digital systems can provide higher image quality and improve processing time, image storage, and image transfer over previously known x-ray film techniques that expose conventional plates. However, digital radiography inspection systems may not be readily equipped for, nor can they operate at, the pressures that occur deep under the ocean surface where the deepwater assets are found. These pressures can, for example, damage equipment and/or induce anomalies in the digital images that degrade the overall image quality of digital radiography imaging systems.

The discussion above is merely provided for general background information and is not intended to be used as an aid in determining the scope of the claimed subject matter.

BRIEF DESCRIPTION OF THE INVENTION

This disclosure describes embodiments of an apparatus, and a system incorporating the apparatus, with a housing that forms a fluid environment about a digital detector that is responsive to radiation. An advantage that the practice of some embodiments of the apparatus is to generate digital images at below the ocean surface and, in particular, find use at depths where deepwater pipes and pipelines are found.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
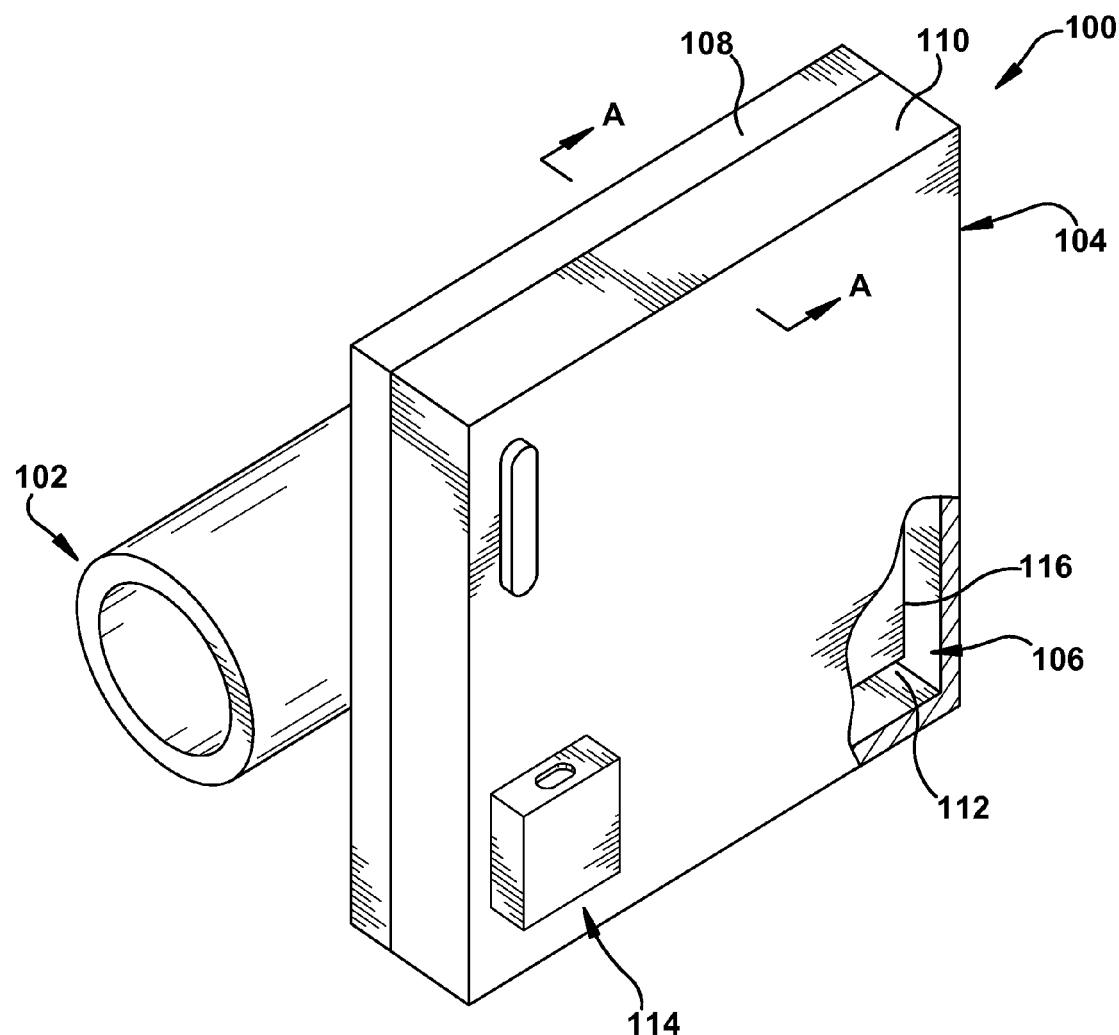
FIG. 1 depicts a perspective view of an exemplary apparatus that can generate digital images in response to radiation.

FIG. 1 depicts a perspective view of an exemplary apparatus 100 that can cooperate with other equipment to generate digital images from radiation sources (e.g., isotope and Betatron radiation sources). The apparatus 100 is suitable for use at subsea depths and in other environments that exhibit relatively high pressures, e.g., depths of 3000 m or more. These digital images can show anomalies in an asset 102, e.g., oil and gas pipes and pipelines. Such anomalies can often lead to structural failure of the asset 102. The apparatus 100 includes a housing 104 that forms a sealed cavity 106. In one construction, the housing 104 includes a front piece 108 and a back piece 110, which couple to one another to hermetically seal and/or make the sealed cavity 106 water-tight. Although not shown, other elements, e.g., seals, gaskets, fasteners, and the like, may find use in construction of the housing 104 to secure its parts (e.g., the front piece 108 and the back piece 110) together.

The apparatus 100 also includes a compensation fluid, generally identified by the numeral 112. The compensation fluid 112 creates a fluidic environment inside of the sealed cavity 106 that is useful to compensate for pressure differentials the apparatus 100 may experience when in position proximate the asset 102. In one embodiment, the apparatus 100 may also include a pressure compensation mechanism 114 that secures to the housing 104. The pressure compensation mechanism 114 couples with the sealed cavity 106 to maintain the pressure of the compensation fluid 112 in the sealed cavity 110. As also shown in FIG. 1, a detector element 116 resides in the sealed cavity 106 to position the detector element 116 in the fluidic environment and effectively immerse the detector element 116 in the compensation fluid 112. The detector element 116 is responsive to radiation from the radiation source, generating in one example, a digital image that can be viewed at a location remote from the detector 116.

The pressure compensation mechanism 114 places the compensation fluid 112 under positive pressure to prevent fluids (e.g., seawater) from penetrating into the sealed cavity 110 in the event of mechanical failure in the housing 104. This features can prevent damage to the detector 116 by allowing sufficient time to remove the apparatus 100 from its deepwater location. In one example, the pressure compensation mechanism 114 includes a bladder in fluid communication with the sealed cavity 106 and a spring or other mechanism that applies a force to the bladder. The bladder can hold a volume of the compensation fluid 112, which flows between the bladder and the sealed cavity 110, e.g., via a piece of tubing and/or conduit secured to the bladder and the housing 104. During operation, pressure acts on the outside of the housing 104 and the bladder, thereby forcing compensation fluid 112 out of the bladder and into the sealed cavity 106. The spring mechanism provides additional spring force, which positively pressurizes the sealed cavity 106, thereby preventing water from entering the sealed cavity in the event of a leak or other failure in the structure of the housing 104 that exposes the sealed cavity 106 to the ambient environment.

Examples of the compensation fluid 112 include oils (e.g., provided by Petro-Rite, Inc. under the Enviro-Rite brand) and, more particularly, include oils, lubricants, and like compositions of various weights and fluidic properties. These compositions may exhibit properties that are acceptable for use in aquatic environments where the asset 102 may be located. It is also desirable that the composition does not interfere with operation of the apparatus 100 to capture digital images of the asset 102. Moreover, use of the composition fluid 112 can dissipate thermal energy. This feature of the compensation fluid 112 can maintain the detector 116 (and its components) at uniform temperature, which improves certain performance characteristics (e.g., image quality) of the detector 116.

The detector element 116 is responsive to radiation that penetrates through the asset 102. In one example, the detector element 116 generates digital signals that, after further processing, render digital images in which anomalies in the asset 102 are visible. While details of the construction of the detector element 116 are found further below, generally the structure of the detector element 116 permits the detector element 116 to operate in the fluidic environment that is found in the sealed cavity 106. Examples of the detector element 116 utilize various sealants that moderate penetration of the compensation fluid 112 into certain areas of the detector element 116, while also preventing such penetration in other areas of the detector element 116. Absence of such sealants may reduce clarity of the resulting digital images. Moreover, construction of the detector element 116 may also forgo use of foams and other porous and semi-porous materials. These materials can deform under pressure, resulting in air pockets that can show up as suspect anomalies in the digital images.

Figure 2:
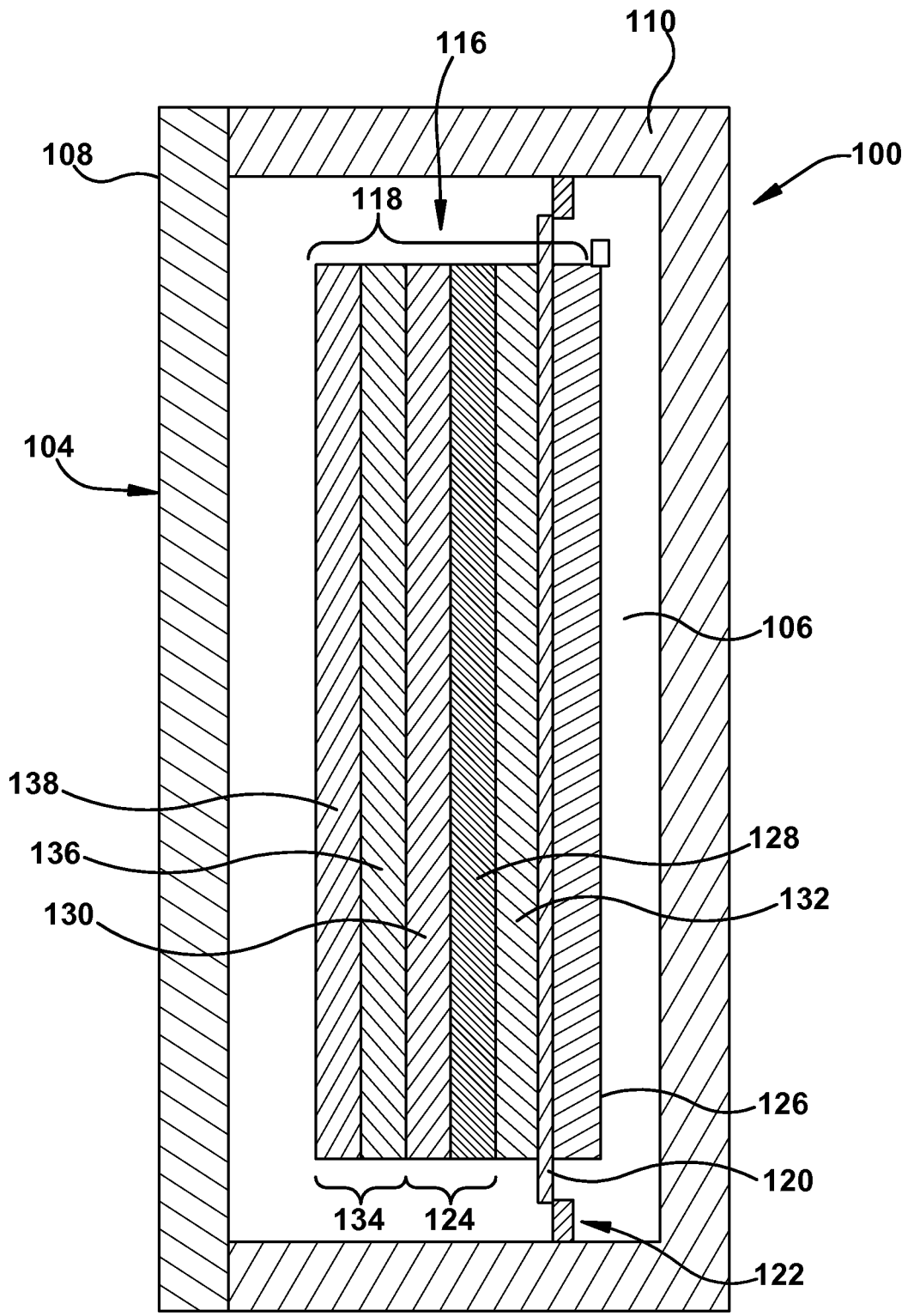
FIG. 2 depicts a cross-section view of the exemplary apparatus of FIG. 1.

FIG. 2 illustrates a cross-section view of the apparatus 100 taken along line A-A of FIG. 1. The view of FIG. 2 shows the interior of the sealed cavity 106 and, more particularly, highlights certain details of the construction of the detector element 116. In one embodiment, the detector element 116 has a layered structure 118 that includes a support panel 120, which in one example comprises aluminum but can also comprise a variety of other materials (e.g., plastics, metals, composites, etc.). The support panel 120 couples with the housing 104 to suspend the detector element 116 within the sealed cavity 106. For example, as shown in FIG. 2, the housing 104 can have one or more boss features 122 that support the support panel 120. The boss features 122 can suspend the detector element 116 within the sealed cavity 106, e.g., in spaced relation from one or more interior surfaces of the sealed cavity 106. In one example, the boss features 122 are located in positions that space the detector element 116 from the front and back interior surfaces of the sealed cavity 106. This disclosure does, however, envisage other configurations of components that can support the detector element 116 within the sealed cavity 106 as contemplated herein.

Other components of the detector element 116 include a photodiode member 124 and an electronics component 126 secured to opposing sides of the support panel 120. The photodiode member 124 includes a glass substrate 128 and a diode layer 130. In one example, a film 132 (e.g., comprising a polyamide material often recognized as KAPTON®) resides between the glass substrate 128 and the support panel 120. Other components of the detector element 116 include a scintillator member 134 that sits on top of the photodiode member 120. The scintillator member 134 can have a scintillator screen member 136 and a protective member 138. The scintillator screen member 136 can comprise comprising a luminescent material and/or material photosensitive to the radiation that impinges thereon. During operation, the scintillator screen member 136 absorbs photons from a radiation source and converts the photons into light photons. The light photons impinge on the photodiode member 124, which converts the light photons to electrical signals. The electrical signals are read out by the electronics component 126. In one example, the electronic component 126 turns the electrical signals into digital data that is sent to an image processor (not shown) for processing, e.g., into digital images.

Figure 3:
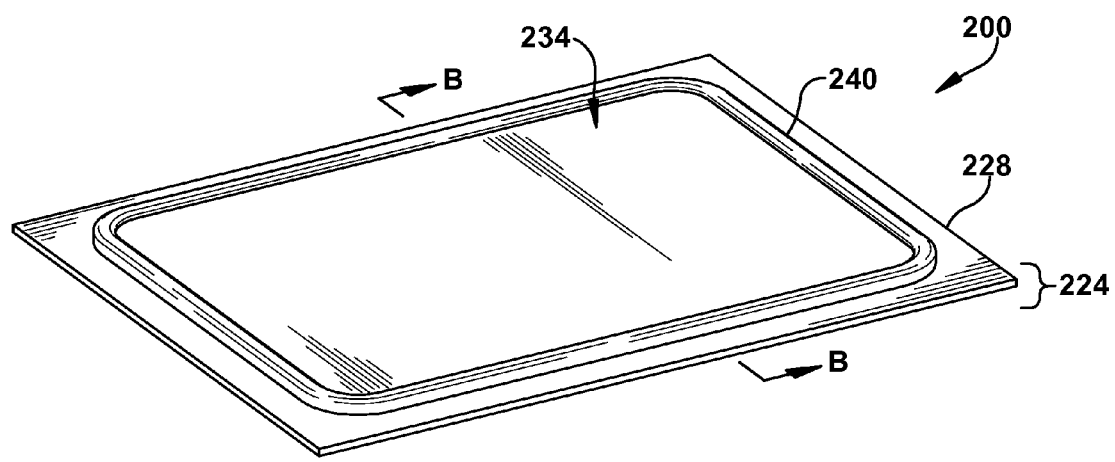
FIG. 3 depicts a perspective view of an exemplary detector for use in the apparatus of FIGS. 1 and 2.
Figure 4:
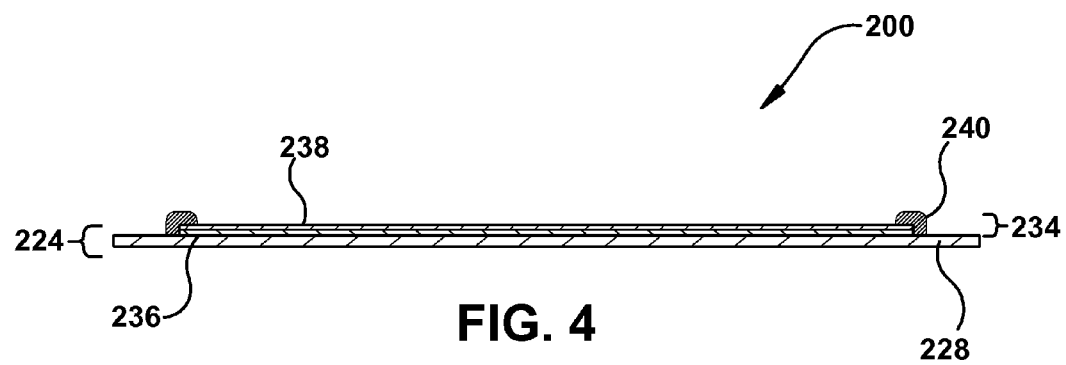
FIG. 4 depicts a cross-section view of the exemplary detector of FIG. 3.

Additional details of embodiments of the apparatus 100 and, more particularly, examples of the detector element 116 are described next in connection with FIGS. 3-6. FIGS. 3 and 4 focus on coupling of a photodiode member and a scintillator member to prevent fluid from migrating between these components and into the scintillator area. FIG. 3, for example, shows a portion of an exemplary detector element 200 that includes a photodiode member 224 with a glass substrate 228. A scintillator member 234 resides on the glass substrate 228. A first seal member 240 circumscribes the periphery of the scintillator member 234 to secure the scintillator member 234 to the glass substrate 228. The first seal member 240 is, in one example, impermeable to fluid and, in particular, arranged as a barrier to prevent migration of the compensation fluid between the scintillator member 234 and the glass substrate 228 as discussed herein.

As best shown in FIG. 4, the scintillator member 234 can include several components, e.g., a scintillator screen member 236 and a protective member 238. The first seal member 240 can cover the peripheral edges of one or more of these components. This configuration of the first seal member 240 can prevent fluid migration between the scintillator member 234 and the glass substrate 228 and between the components of the scintillator member 234. In one example, a portion of the first seal member 240 is disposed on the glass substrate 228 and a portion of the first seal member 240 is dispose on the scintillator member 234. While these portions can vary in size, the present disclosure contemplates at least one configuration in which 50% of the material of the first seal member 240 may reside on the glass substrate 228 and 50% of the material of the first seal member 240 may reside on the scintillator member 234.

Figure 5:
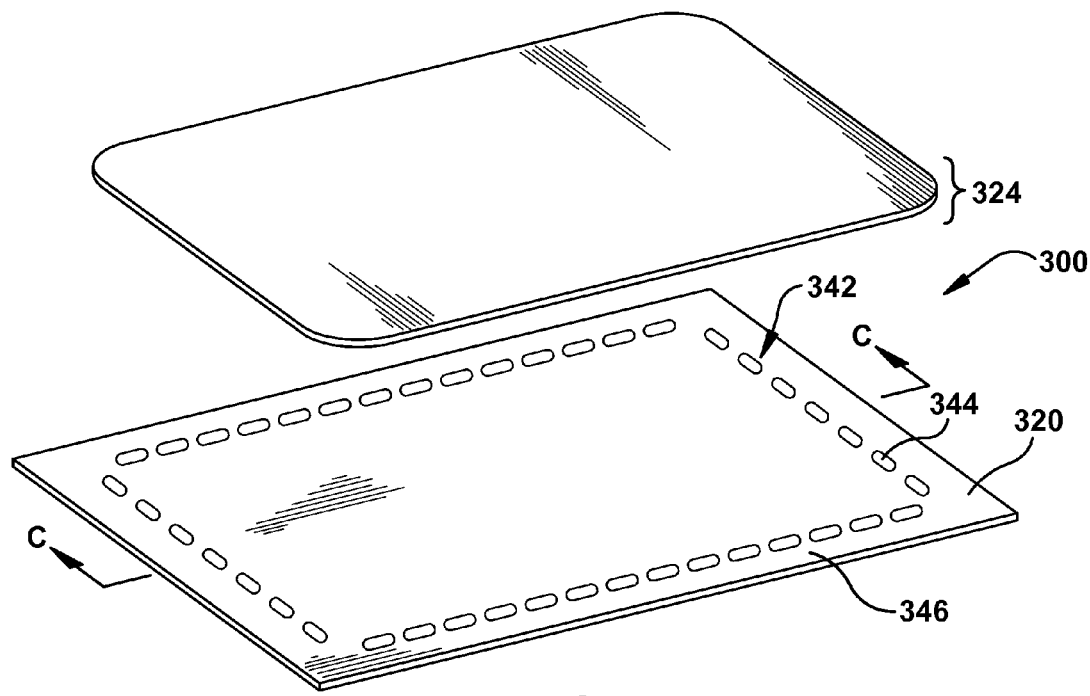
FIG. 5 depicts a perspective, exploded, assembly view of an exemplary detector for use in the exemplary apparatus of FIGS. 1 and 2.
Figure 6:
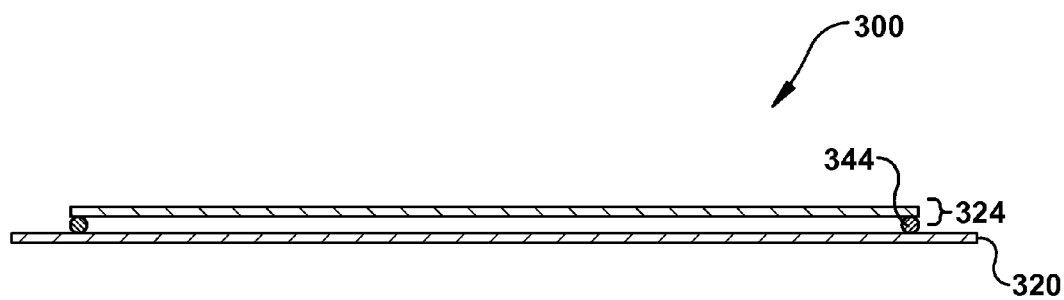
FIG. 6 a cross-section, assembled view of the exemplary detector of FIG. 5.

FIG. 5 depicts a portion of an exemplary detector element 300 with a support plate 320 and a photodiode member 324. The detector element 300 also includes a second seal member 342 that traverses the surface of the support plate 320. The second seal member 342 includes a plurality beads 344 and intervening gaps 346, which collectively circumscribe a shape on the support plate 320 sufficient to secure the photodiode member 324 to the support plate 320. As best shown in FIG. 6, in one example, the photodiode member 324 rests on top of the beads 344 to effectively secure the photodiode member 324 to the support plate 320.

Examples of materials for use as the first seal member 240 and the second seal member 342 include silicone compounds and other materials that the exhibit properties to permit operation of the first seal member 240 and the second seal member 342 as discussed herein. Selection of these material may take into account the composition of the compensation fluid, and vice versa, to avoid premature break-down that will dissipate sealing and adhesive capabilities of the first seal member 240 and the second seal member 342.

Figure 7:
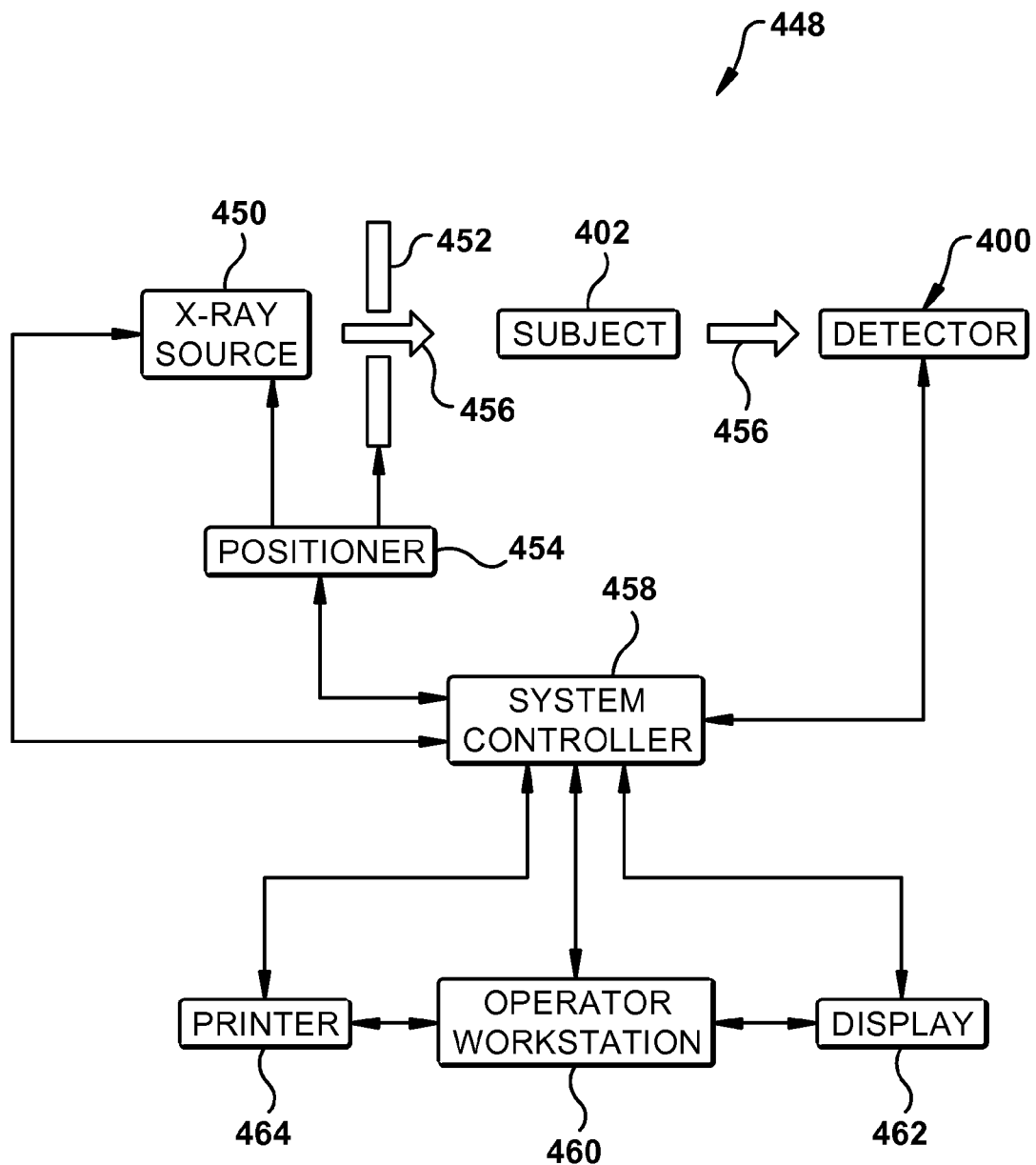
FIG. 7 depicts a block diagram of a digital imaging system that can incorporate the exemplary apparatus of FIGS. 1 and 2.

FIG. 7 depicts another exemplary apparatus 400 that can capture images of an asset 402 as part of a digital imaging system 448. One or more of the elements that are discussed below may be omitted and/or modified to permit implementation of the digital imaging system 448 for inspecting deepwater assets. In one embodiment, the digital imaging system 448 includes a radiation source 450 (e.g., an isotope source and/or a Betatron source), a collimator 452 adjacent the radiation source 450, and a positioner 454. The positioner 454 can be a mechanical controller coupled to radiation source 448 and collimator 452 for controlling the positioning of radiation source 448 and collimator 452.

The digital imaging system 448 is designed to create images of the asset 402 by means of radiation and, as shown in the example of FIG. 7, a radiation beam 456 emitted by radiation source 450, and passing through collimator 452, which forms and confines the radiation beam 456 to a desired region, wherein the asset 402, e.g., a deepwater pipeline is positioned. A portion of the radiation beam 456 passes through or around the asset 402, and being altered by attenuation and/or absorption, continues on toward and impacts the apparatus 400. As discussed above, the apparatus 400 converts photons received on its surface to lower energy light photons, and subsequently to electric signals, which are acquired and processed to reconstruct an image of internal structure within the asset 402.

The digital radiography imaging system 448 further includes a system controller 458 coupled to radiation source 450, positioner 454, and apparatus 400 for controlling operation of the radiation source 450, positioner 454, and apparatus 400. The system controller 458 may supply both power and control signals for imaging examination sequences. In general, system controller 458 commands operation of the radiography system to execute examination protocols and to process acquired image data. The system controller 458 may also include signal processing circuitry, based on a general purpose or application-specific computer, associated memory circuitry for storing programs and routines executed by the computer, as well as configuration parameters and image data, interface circuits, and so forth.

The system controller 458 may further include at least one processor designed to coordinate operation of the radiation source 450, positioner 454, and apparatus 400, and to process acquired image data. The at least one processor may carry out various functionality in accordance with routines stored in the associated memory circuitry. The associated memory circuitry may also serve to store configuration parameters, operational logs, raw and/or processed image data, and so forth. In an exemplary embodiment, the system controller 458 includes at least one image processor to process acquired image data.

The system controller 458 may further include interface circuitry that permits an operator or user to define imaging sequences, determine the operational status and health of system components, and so-forth. The interface circuitry may allow external devices to receive images and image data, and command operation of the radiography system, configure parameters of the system, and so forth.

The system controller 458 may be coupled to a range of external devices via a communications interface. Such devices may include, for example, an operator workstation 460 for interacting with the digital imaging system 448, processing or reprocessing images, viewing images, and so forth. In the case of tomosynthesis systems, for example, the operator workstation 460 may serve to create or reconstruct image slices of interest at various levels in the subject based upon the acquired image data. Other external devices may include a display 462 or a printer 464. In general, these external devices 458, 462, 464 may be local to the image acquisition components, or may be remote from these components, e.g., on a ship or derrick, or in an entirely different location, linked to the image acquisition system via one or more configurable networks, such as the Internet, intranet, virtual private networks, and so forth. Such remote systems may be linked to the system controller 458 by any one or more network links. It should be further noted that the operator workstation 460 may be coupled to the display 462 and printer 464, and may be coupled to a picture archiving and communications system (PACS). Such a PACS might be coupled to remote clients, such as a engineering department information systems, or to an internal or external network, so that others at different locations may gain access to image data.

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for inspecting assets in high pressure environments, said apparatus comprising:
a housing with a sealed cavity;
a compensation fluid disposed in the sealed cavity; and
a detector element immersed in the compensation fluid, the detector element comprising,
a glass substrate,
a scintillator member coupled to the glass substrate, and
a first seal member disposed about and in contact with the peripheral edges of the scintillator member to secure the scintillator member to the glass substrate,
wherein the first seal member is impermeable to the compensation fluid.

2. The apparatus of claim 1, wherein the compensation fluid comprises hydraulic oil.

3. The apparatus of claim 1, wherein the compensation fluid has a composition that is configured to dissipate thermal energy from the detector element in the fluidic environment.

4. The apparatus of claim 1, wherein the detector element further comprises a support plate coupled to the glass substrate, and wherein, when the detector element is positioned in the sealed cavity, the support plate is disposed on a feature of the housing to suspend the detector element within the compensation fluid.

5. The apparatus of claim 1, wherein the scintillator member comprises a scintillator screen member and a protective member disposed on an exposed side of the scintillator screen member, and wherein the first seal member is configured to prevent compensation fluid from flowing between the scintillator screen member and the protective member.

6. The apparatus of claim 1, wherein the first seal member comprises silicone rubber.

7. The apparatus of claim 1, wherein the sealant comprises RTV silicone sealant.

8. The apparatus of claim 1, further comprising a pressure compensation mechanism coupled to the housing, wherein the housing is configured to allow compensation fluid to flow between the pressure compensation mechanism and the sealed cavity.

9. The apparatus of claim 8, wherein the pressure compensation mechanism is configured to maintain the compensation fluid in the sealed cavity under positive pressure.

10. An apparatus, comprising:
a housing with a sealed cavity;
a compensation fluid disposed in the sealed cavity; and
a detector element immersed in the compensation fluid, the detector element comprising,
a glass substrate,
a scintillator member coupled to the glass substrate, and
a first seal member disposed about the peripheral edges of the scintillator member to secure the scintillator member to the glass substrate,
wherein the detector element further comprises a support plate coupled to the glass substrate,
wherein, with the detector element in position in the sealed cavity, the support plate is disposed on a feature of the housing to suspend the detector element within the compensation fluid,
wherein the detector element includes a second seal member to secure the glass substrate to the support plate,
wherein the first seal member is impermeable to the compensation fluid, and
wherein the second seal member is permeable to the compensation fluid.

11. An apparatus for generating digital images in response to radiation, said apparatus comprising:
a housing configured to retain a compensation fluid to form a fluidic environment;
a detector element disposed in the fluidic environment, the detector element comprising,
a scintillator member,
a photodiode member with a glass substrate, and
a first seal member configured to secure the scintillator member to the glass substrate, the first seal member disposed about and in contact with the periphery of the scintillator member to form a barrier that is impermeable to fluid; and
a pressure compensation mechanism in fluid connection with the fluidic environment, the pressure compensation mechanism configured to maintain the compensation fluid in the fluidic environment under positive pressure.

12. The apparatus of claim 11, wherein the detector element further comprises:
a support panel; and
a second seal member configured to secure the glass substrate to the support panel.

13. An apparatus, comprising:
a housing configured to retain a compensation fluid to form a fluidic environment;
a detector element disposed in the fluidic environment, the detector element comprising,
a scintillator member,
a photodiode member with a glass substrate,
a support panel,
a first seal member configured to secure the scintillator member to the glass substrate, the first seal member disposed about the periphery of the scintillator member and configured to form a barrier that is impermeable to fluid,
a second seal member configured to secure the glass substrate to the support panel; and
a pressure compensation mechanism in fluid connection with the fluidic environment, the pressure compensation mechanism configured to maintain the compensation fluid in the fluidic environment under positive pressure,
wherein the second seal member comprises a plurality of beads and intervening gaps between the plurality of beads.

14. The apparatus of claim 12, wherein the detector element further comprises a film between the glass substrate and the support panel.

15. The apparatus of claim 11, wherein the scintillator member comprises a scintillator screen member and a protective member disposed thereon, and wherein the first seal member is configured to prevent the compensation fluid from penetrating between the scintillator screen member and the protective member and between the scintillator screen member and the glass substrate.

16. A digital imaging system compatible with high-pressure environments found underwater, said digital imaging system comprising:

a device configured to generate radiation; and
an apparatus configured to generate digital images in response to the radiation, the apparatus comprising,
a housing,
a compensation fluid inside of the housing, and
a detector element immersed in the compensation fluid, the detector element comprising a layered structure with a first seal member configured to prevent the compensation fluid to flow into the interior of the detector element and a second seal member comprising a plurality of beads and intervening gaps between the plurality of beads that configure the second seal member to permit the compensation fluid to flow into the interior of the detector element.

17. The digital imaging system of claim 16, wherein the compensation fluid is under positive pressure in the housing.

18. The digital imaging system of claim 16, wherein the detector element further comprises a scintillator and photodiode member, and wherein the first seal member is configured to secure the scintillator member to the photodiode member of the detector element.

19. The digital imaging system of claim 18, wherein the detector further comprises a support panel, wherein the second seal member is configured to secure the photodiode member to the support panel, and wherein the support panel couples with the housing to position the detector element in a spaced relation from interior surfaces of the housing.

20. The digital imaging system of claim 16, wherein the first seal member and the second seal member comprise RTV silicone sealant.

* * * * *

UNITED STATES PATENT AND TRADEMARK OFFICE
CERTIFICATE OF CORRECTION

| | | |
|---|---|---|
| PATENT NO. | : 8,822,932 B2 | Page 1 of 1 |
| APPLICATION NO. | : 13/351876 | |
| DATED | : September 2, 2014 | |
| INVENTOR(S) | : Scoville et al. | |

It is certified that error appears in the above-identified patent and that said Letters Patent is hereby corrected as shown below:

In the Claims

A typographical error has been found in claim 9, Col. 7, lines 53-55, please change to the following:

The apparatus of claim 8, wherein the pressure compensation mechanism is configured to maintain the compensation fluid in the sealed cavity under positive pressure.

Signed and Sealed this
Thirteenth Day of January, 2015

Michelle K. Lee
*Deputy Director of the United States Patent and Trademark Office*